United States Patent [19]
Aldinger

[11] 3,952,744
[45] Apr. 27, 1976

[54] TAPE ATTACHMENT SYSTEM FOR DISPOSABLE DIAPERS

[75] Inventor: Karl E. Aldinger, Appleton, Wis.

[73] Assignee: Kimberly-Clark Corporation, Neenah, Wis.

[22] Filed: Mar. 28, 1975

[21] Appl. No.: 562,926

[52] U.S. Cl............................ 128/287; 128/284
[51] Int. Cl.².................. A61F 13/16; A41B 13/02
[58] Field of Search.......... 128/284, 287; 24/73 VA, 24/DIG. 11

[56] References Cited
UNITED STATES PATENTS

| | | | |
|---|---|---|---|
| 3,900,031 | 8/1975 | Endres | 128/287 |
| 3,901,239 | 8/1975 | Tritsch | 128/287 |

Primary Examiner—Aldrich F. Medbery
Attorney, Agent, or Firm—Daniel J. Hanlon, Jr.; William D. Herrick; Raymond J. Miller

[57] ABSTRACT

A pressure sensitive tape attachment system for disposable diapers in which the strippable protective release sheet for the pressure sensitive tape has one end permanently secured to the outer or non-body contacting surface of the diaper. The protective sheet remains attached to the outer surface of the diaper when the latter is worn.

5 Claims, 7 Drawing Figures

TAPE ATTACHMENT SYSTEM FOR DISPOSABLE DIAPERS

BACKGROUND OF THE INVENTION

Most disposable diapers now manufactured and sold are provided with a pressure sensitive tape at each of the corners adjacent one end of the diaper for securing the diaper together at the waist of the child in the diapering process. One end portion of such tape is commonly attached to the back side of the diaper while the pressure sensitive adhesive surface on the other free end portion is covered with a strippable release-coated protective sheet which is removed from the tape when the diaper is applied to the child. It is preferred that the strippable protective sheet be disposed in such a manner that it will remain attached to the diaper after the pressure sensitive adhesive on the free end portion of the tape is uncovered when preparing the tape for its fastening function. In all of the known embodiments wherein the protective sheet is so disposed as to remain attached either directly to the diaper or to the tape itself after the pressure sensitive surface is uncovered, the protective sheet is situated on the body-contacting side of the diaper. Since the surface of the protective sheet is usually non-breathable and has a release coating, it can become a source of discomfort and possible irritation where it contacts the skin. Accordingly, it would be desirable to find a way to eliminate this problem.

This invention is directed towards solving that problem by providing a pressure tape fastening system in which the releasable protective sheet has one end permanently attached to the outside surface of the diaper rather than to the inside surface. The disposition of the protective sheet is so arranged that when it is stripped from the tape it will remain on the outside of the diaper to assure that it will not contact the infant's skin when the diaper is worn.

SUMMARY OF THE INVENTION

An important object of this invention is to provide a tape fastening system in which the protective cover sheet for the adhesive area of pressure sensitive fastening tapes remains attached to the diaper after the pressure sensitive surface is uncovered, and which protective sheet is so disposed that it will not contact the infant's skin while the diaper is worn.

In the improved fastening system, one end portion of the fastening tape is attached to the backing sheet at one corner of the diaper and the other free end is adapted to extend beyond the edge of the diaper for fastening purposes in the usual manner. In accordance with this invention, the free end portion of the tape is folded back on itself with the non-adherent surfaces in contact, and the pressure-sensitive adhesive surface of the folded over free end portion of the tape is releasably covered by an elongate release-coated protective sheet. A section of the elongate release-coated protective sheet extends beyond the free end of the tape and a terminal portion of the protective sheet is permanently secured to the backing sheet. Either the release-coated side or the non-release-coated side of the protective sheet may be secured to the backing sheet. In an additional embodiment a low tack area of adhesive may be disposed on the back side of the diaper to receive and hold the free end of the protective sheet after it has been stripped from the pressure sensitive tape preparatory to applying the diaper to the child.

Other embodiments and advantages of the invention will become apparent by reference to the accompanying drawings and the following detailed description.

DETAILED DESCRIPTION OF THE DRAWINGS AND PREFERRED EMBODIMENTS OF THE INVENTION

Figure 1:
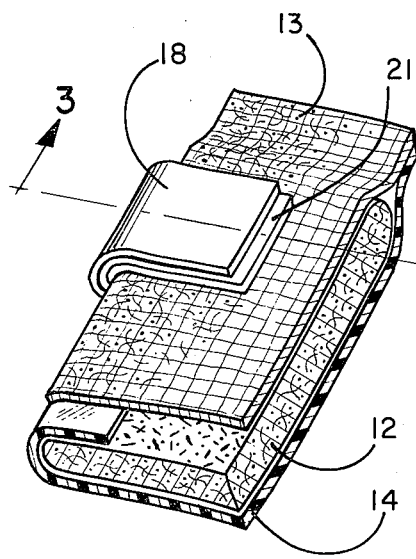
FIG. 1 is a fragmentary perspective view of a corner of the body-contacting side of a diaper utilizing a prior art tape fastening system.

Most conventional disposable diapers commonly comprise a flat rectangular pad of absorbent material such as an air-formed batt of wood pulp fibers known as fluff, or multiple plies of cellulose wadding, and the like, with a fluid-pervious cover sheet of non-woven material on the top body-contacting surface and a fluid-impervious backing sheet of thin plastic film on the back or outer surface. A variety of edge structures are utilized at the side and ends of the diaper to maintain these elements in unitary assembly and this invention is not intended to be limited only to diapers with the side and end structures illustrated in the drawings. The finished diapers are often provided with a variety of folding arrangements adapted to improve fit, handling, packaging, and the like. An increasing number of the various styles of disposable diapers are also being provided with pressure-sensitive tape means for fastening the diaper at the waist in place of safety pins or the like.

This invention is readily adaptable for use with all of such forms of disposable diapers which can use pressure-sensitive tape fastening means, and is directed particularly to the particular arrangement of the protective cover sheet, which sheet is stripped from the tape's pressure-sensitive adhesive surface prior to use when applying the diaper.

Figure 2:
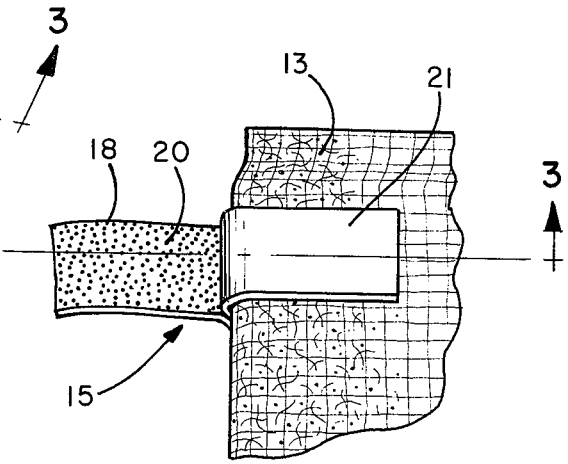
FIG. 2 is a fragmentary plan view of the FIG. 1 tape fastening system in which the free end of the tape has been stripped from its protective covering sheet preparatory to applying the diaper to a child.
Figure 3:
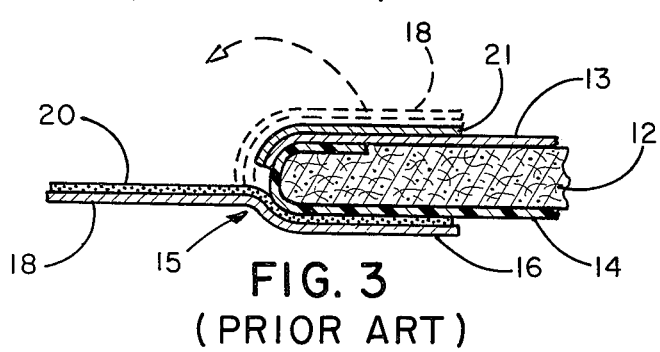
FIG. 3 is a section taken along lines 3—3 of FIGS. 1 and 2.

Referring now to the drawings, FIGS. 1, 2, and 3 are fragmentary showings of a corner portion of a disposable diaper in which the tape attachment system is made in accordance with a typical prior art structure. Such diapers typically comprise an absorbent core 12, a fluid pervious cover sheet 13, and a fluid impervious backing sheet 14. A number of variations of each of these structural elements of disposable diapers are well known in the art and need no further detailing here since the invention is directed to the tape fastening system rather than to the particular diaper structure. It is understood, of course, that while only one corner of the diaper is shown in the drawings, the diaper will have a similar structure, including a tape fastening means, at its opposite corner.

The pressure-sensitive tapes commonly used for fastening purposes comprise strong flexible base sheet materials such as plastic film or resin-impregnated paper coated on one surface with a pressure-sensitive adhesive and on the other surface with a release coating. The release coat is necessary, of course, to permit the tape to be unwound from the roll form in which it is usually supplied for manufacturing purposes, unless the roll has a separate removable liner provided; the latter being a relatively expensive form not often used.

Referring again to FIGS. 1–3, a first end portion 16 of a pressure-sensitive tape strip 15 is fastened to a marginal area of backing sheet 14 near one corner of the diaper. The second or free end portion 18 of tape strip 15 is adapted to extend beyond diaper edge 17 and is temporarily positioned in releasable association with a release-coated protective sheet 21. End portion 18 is used to fasten the ends of the diaper together at the waist in place of conventional old fashioned safety pins.

In this prior art embodiment, end portion 18 of the tape is stripped from its temporary position in adherent contact with release-coated protective sheet 21 to expose pressure-sensitive adhesive 20 and the tape is pulled out to its extended position as shown in FIGS. 2 and 3 where it is ready for the fastening function.

As shown in the drawings which represent prior art, release-coated protective sheet 21 remains in position on the body-contacting surface of cover sheet 13 where it can easily come into contact with the skin of the child, which is undesirable as noted above.

In the improved construction of this invention as shown in FIGS. 4–7, the protective sheet 21a and 21b is so disposed that it will remain attached to backing sheet 14 by being permanently secured thereto at its terminal portion 30 by means of an adhesive 31.

Figure 4:
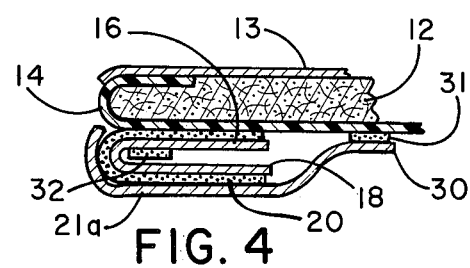
FIG. 4 is a section similar to FIG. 3 but showing one embodiment of the tape fastening system of this invention.

As shown in FIG. 4, when the tape 15 is in its temporary storage position, as packaged, the first end portion 16 of the tape is attached to the backing sheet 14 as in the conventional structure. The free end 18 of the tape is folded back onto the first end portion 16 while held by adhesive 32 and in that position is temporarily covered by protective sheet 21a which has its terminal end 30 secured permanently to backing sheet by adhesive 31. When the diaper is readied for use, sheet 21a is pulled off of pressure sensitive adhesive 20 and the free end of the tape is extended outboard of the diaper edge as shown in FIG. 5 where it is ready for its fastening function.

The free end of the release sheet may be allowed to hang free, or if a neater arrangement is wanted, a small spot of low tack adhesive may be provided as shown at 32, located between the folded over portions of the tape. When the tape is stretched out for use, the free end of protective sheet 21a may then be adhered to that adhesive area as shown in FIG. 5.

Figure 5:
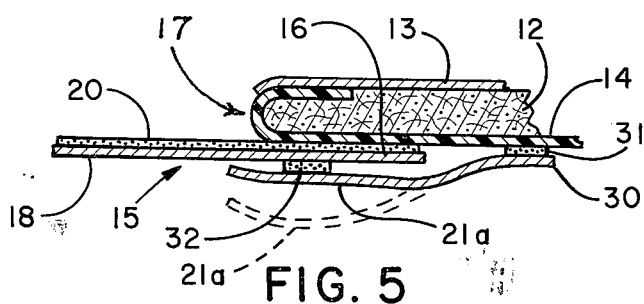
FIG. 5 shows that FIG. 4 section in which the protective covering sheet has been stripped from the tape and the tape is in position for its fastening function.
Figure 6:
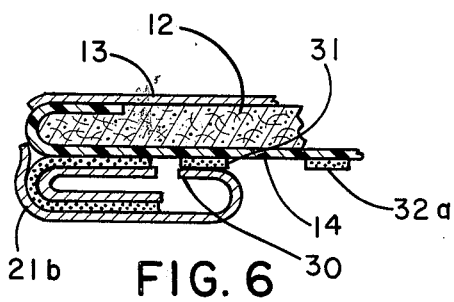
FIG. 6 is a section similar to FIG. 4 showing another embodiment of the invention.
Figure 7:
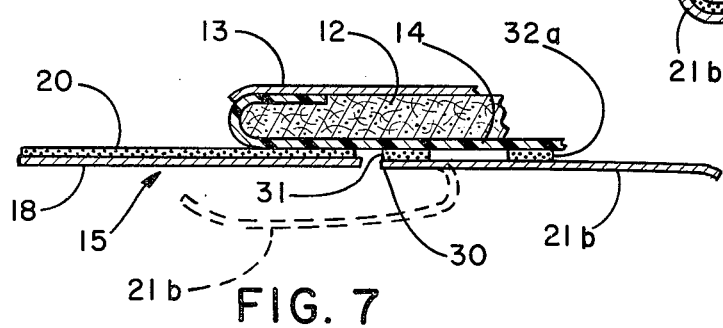
FIG. 7 shows the FIG. 6 section preparatory to applying the diaper to a child.

FIGS. 6 and 7 are much the same as FIGS. 4 and 5 except that in this instance, protective sheet 21b has its non-release-coated side rather than its release-coated side, attached at its terminus 30 to the backing sheet 14 by adhesive spot 31. In this embodiment the spot of adhesive 32a is positioned on the backing sheet toward the inner area of the backing sheet rather than on the tape itself.

In either case, the protective cover sheet is so disposed in its permanent attachment so that it will not contact the child's skin when the diaper is worn.

What is claimed is:

1. In a tape fastening system for a disposable diaper which has pressure-sensitive adhesive fastening tapes disposed at opposite corners of one end thereof for fastening the diaper about the waist, wherein said diaper comprises an absorbent core disposed between a bottom backing sheet and a top body-contacting cover sheet, wherein said tape has pressure sensitive adhesive on one surface, and wherein one end portion of said tape has a surface permanently attached to said backing sheet near one corner of the diaper and an opposite non-adhering surface the other end portion of the tape is free and has a length to extend beyond the edge of said diaper, the improvement comprising a means for holding said tape wherein said free end portion is folded back over the attached end portion of said tape with the non-adherent surfaces of the tape in contact and the pressure sensitive adhesive surface of said folded-over free end portion is releasably covered by an elongate release-coated protective sheet, a section of said protective sheet having a portion extending beyond the folded portion of said tape and a terminal portion of said protective sheet being permanently secured to said backing sheet.

2. The tape fastening system of claim 1 wherein the backing sheet of said diaper is provided with a small area of low tack adhesive positioned to receive and hold the unsecured end of said protective sheet after said sheet is stripped from said tape.

3. The tape fastening system of claim 2 wherein the release-coated side of the terminal portion of said protective sheet is the side secured to said backing sheet.

4. The tape fastening system of claim 2 wherein the non-release-coated side of the terminal portion of said protective sheet is the side secured to said backing sheet.

5. The tape fastening system of claim 4 wherein said area of low tack adhesive is disposed on the non-adherent surface of the tape located between the folded over portions of said tape.

* * * * *